United States Patent [19]
Kieft

[11] Patent Number: 5,169,783
[45] Date of Patent: Dec. 8, 1992

[54] INCREASING NUCLEATION ACTIVITY WITH LICHENS AND FUNGI

[75] Inventor: Thomas L. Kieft, Socorro, N. Mex.

[73] Assignee: New Mexico Tech Research Foundation, Socorro, N. Mex.

[21] Appl. No.: 260,252

[22] Filed: Oct. 20, 1988

[51] Int. Cl.$^5$ .................... C12N 1/00; C12N 1/12; C12N 1/14; F25C 1/02
[52] U.S. Cl. .................. 435/317.1; 239/2.2; 435/254; 435/257
[58] Field of Search .............. 435/254, 257, 317.1, 435/252.3, 69.1, 172.3, 320; 239/2.2, 2.1

[56] References Cited

U.S. PATENT DOCUMENTS 4,784,943 11/1988 Warren et al. .................. 435/7.32

OTHER PUBLICATIONS

Abstract entitled "Determinants of Environmental Stree Tolerance of *Pseudomonas Syringae* on Leaves" by S. E. Lindow, et al. from handouts of seminar entitled Ice Nucleation Conference, Jun. 18-21, 1989, Saskatoon, Saskatchewan Canada.

Abstract entitled "Preliminary Experimental Evaluation of SNOMAX Snow Inducer *Pseudomonas Syringae* as an Artificial Ice Nucleus for Westher Modification" from handouts of seminar entitled Ice Nucleation Conference, Jun. 18-21, 1989, Saskatoon, Saskatchewan Canada.

Abstract of paper written by D. A. Baertlein, et al., from handouts of seminar entitled "Ice Nucleation Conference", Jun. 18-21, 1989, Saskatoon, Saskatchewan Canada.

Chapter 18 Lichens, from "Experimental Microbial Ecology" by R. Burns, et al. (eds.) (1982) Blackwell, Oxford text, pp. 291-319; (particularly p. 307).

Chapter 2 *Isolation and Nature of Lichen Symbionts*, from "The Lichen Symbiosis", by V. Ahmadjian, (1967), Blaisdell Publishing Company, text, pp. 7-35 and pp. 119-121; (particularly p. 27).

Chapter X *Lichens*, from "Methods in Microbiology", vol. 4 by Norris et al. (1971), Academic Press, New York, Text, pp. 267-293; (particularly p. 269).

"Characterization of Biological Ice Nuclei from a Lichen", by T. L. Kieft, et al. *Journal of Bacteriology*, pp. 3519-3523, Jun. 1990.

"Ice Nucleation Activity in Lichens" by T. L. Kieft *Applied Environmental Microbiology*, pp. 1678-1581 Jul. 1988.

"Molecular Sizes of Lichen Ice Nucleation Sites Determined by Gamma Radiation Inactivation Analysis" by T. L. Kieft et al, submitted to *Cryobiology*, Jun. 26, 1991.

*Primary Examiner*—Richard A. Schwartz
*Assistant Examiner*—Nancy T. Vogel
*Attorney, Agent, or Firm*—Deborah A. Peacock; Donovan F. Duggan

[57] ABSTRACT

The disclosure is directed to increasing ice nucleation activity of liquids and gases by using lichens, fungi, and ice nuclei derived from lichen fungi. The invention is particularly useful for snowmaking, cloud seeding, and other industrial freezing and cooling processes.

12 Claims, 2 Drawing Sheets

500
INCREASING NUCLEATION ACTIVITY WITH LICHENS AND FUNGI

BACKGROUND OF THE INVENTION

1. Field of the Invention

This invention relates to increasing ice nucleation activity by using fungi, lichens, and ice nuclei derived from lichen fungi.

2. Description of the Prior Art

It is desirable to increase ice nucleation activity for certain applications and thereby form ice from liquid or gas at higher temperatures.

Such applications include snowmaking for ski areas, rainmaking or cloud seeding (although currently out of favor in the scientific community), and cooling or refrigerating procedures in industrial applications, etc.

In the absence of heterogeneous ice nuclei, water typically supercools to temperatures well below 0° C. It is not uncommon for supercooling to proceed to −20° C. or lower before freezing occurs. Nuclei present in the water, such as inorganic and organic dust particles, including clay minerals, enable the water to freeze at higher temperatures, e.g. at −10° C. It is desirable to introduce nuclei which will cause the water or liquid to freeze at temperatures such as −5° C. or even higher.

Bacteria have been developed in the art to increase the nucleation activity and thereby allow freezing to occur at higher temperatures, e.g. −5° C. to −1° C. These bacteria are primarily ice nucleation-active (INA) bacteria which occur on crop and wild plants, e.g., INA strains of *Pseudomonas syringae* and *Erwinia herbicola*. However, bacterial ice nuclei are very heat sensitive and thus have a short shelf life. An example of using such bacteria is disclosed in U.S. Pat. No. 4,200,228, entitled SNOW MAKING, to Woerpel. Although the Woerpel patent uses the term "microorganisms," it discloses only bacteria to make snow. There is no teaching of ice nucleation associated with lichens or lichen fungi.

Bacteria have also been used to reduce frost damage to plants by inhibiting rather than increasing nucleation activity. See Anderson, et al, "Reduction of Bacterially Induced Frost Damage to Tender Plants," *J. Amer. Soc. Hort. Sci.*, vol. 109(3), pp. 401–405 (1984); U.S. Pat. Nos. 4,045,910, entitled METHOD FOR REDUCING FROST DAMAGE OF PLANTS, to Arny; et al.; U.S. Pat. No. 4,161,084, entitled METHOD FOR REDUCING TEMPERATURE AT WHICH PLANTS FREEZE, to Arny, et al.; U.S. Pat. No. 4,375,734, entitled PROTECTION OF PLANTS AGAINST FROST INJURY USING ICE NUCLEATION-INHIBITING SPECIES-SPECIFIC BACTERIOPHAGES, to Kozloff, et al.; and U.S. Pat. No. 4,432,160, entitled MICROORGANISM INHIBITION OF FROST DAMAGE TO PLANTS, to Lindow. Chlorella (algae) in an aqueous suspension have also been used in the art to prevent frost damage to plants (see Russian Patent SU 650,558).

No attempts have been made in the art to utilize fungi or lichens to increase ice nucleation activity.

SUMMARY OF THE INVENTION

In accordance with the invention, a method is provided for increasing ice nucleation activity of a liquid or gas. The method comprises the steps of: a) obtaining at least one lichen, fungus, fungus derived from a lichen, microbe comprising genes cloned from a lichen, microbe comprising genes cloned from a fungus, and/or microbes comprising genes cloned from a fungus derived from a lichen (hereinafter "selected suitable member"; and b) adding the selected suitable member to the liquid or gas. The selected suitable member is preferably homogeneously added to the liquid or gas, such as by grinding it before adding it to the liquid or gas. The method of the invention is useful for increasing ice nucleation in aqueous and non-aqueous solutions, suspensions, and homogenates.

The preferred lichens and lichen fungi, useful in accordance with the invention, include the genera Rhizoplaca, Xanthoparmelia, Xanthoria, Platismatia, Acarospora, Leptogium, Psora, Letharia, Peltigera, and Usnea. The preferred fungi, useful in accordance with the invention, include an Antarctic endolith, Rhizoplaca Cladonia, Pertussaria, Lecanora, Phaeographis, and Acarospora.

In the method of the invention, the temperature of the liquid or gas containing the selected suitable member is lowered to a sufficient temperature until ice nucleation activity occurs. This temperature is substantially above the temperature at which ice nucleation activity occurs for the liquid or gas without the selected suitable member. For an aqueous solution, the ice nucleation activity is preferably above approximately −10° C., and most preferably above approximately −5° C.

The selected suitable member preferably has a nuclei density of above approximately $1 \times 10^3$ nuclei per gram.

The method of the invention is useful for snowmaking. The selected suitable member is added to water, and the water temperature is lowered to a sufficient temperature and for a sufficient time for nucleation activity to occur and thereby produce snow. In one preferred method of snowmaking, the selected suitable member is ground and slurried and the slurry is injected into a stream of water droplets produced by a snowmaking machine. In an alternative method of snowmaking, the selected suitable member is ground and added to a stream of water prior to aerosolization in the snowmaking machine.

The method of the invention is also useful for cloud seeding, and other industrial freezing and cooling processes. For cloud seeding, the selected suitable member is added to air at an altitude which is sufficient for nucleation activity to occur and thereby cause rain to form.

The invention also relates to a microbe useful for increasing nucleation activity. This microbe comprises a gene cloned from at least one lichen, fungus, or fungus derived from a lichen.

A primary object of the present invention is to provide fungi, lichens, nuclei extracted from lichen fungi, or nuclei produced from the introduction of lichen fungus genes into bacteria, yeasts, or other microorganisms for increasing ice nucleation activity.

Another object of the present invention is to provide fungi, lichens, nuclei extracted from lichen fungi, or nuclei produced from the introduction of lichen fungus genes into bacteria, yeasts, or other microorganisms for certain applications, including snowmaking, rainmaking, and industrial freezing processes.

An advantage of the present invention is that lichens and associated lichen-derived nuclei can be stored for long periods prior to use in ice nucleation activities.

Other objects, advantages and novel features, and further scope of applicability of the present invention will be set forth in part in the detailed description to follow, taken in conjunction with the accompanying drawing, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention.

DESCRIPTION OF THE PREFERRED EMBODIMENTS OF THE INVENTION

Figure 1:
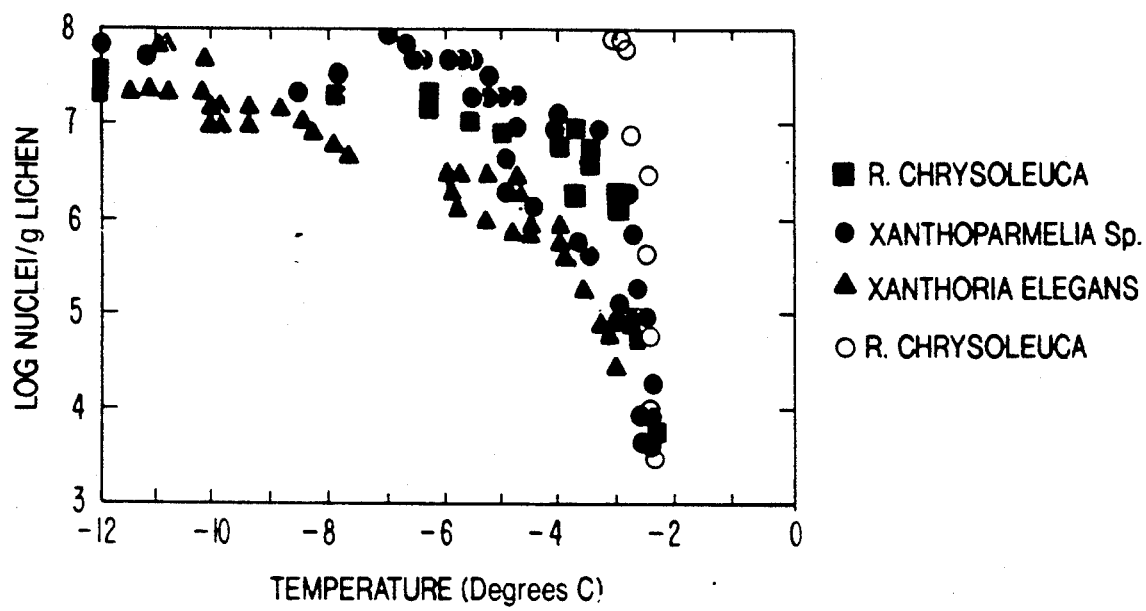
FIG. 1 is a graph of the ice nucleation spectra of certain lichens with high ice nucleation activities.

In accordance with the invention, nucleation activity is increased by the use of fungi, lichens, and/or ice nuclei derived from lichen fungi. Applications in which an increased nucleation activity is desired include, but are not limited to, snowmaking, cloud seeding, and other industrial cooling or freezing applications.

Many fungi and lichens are both frost tolerant and dependent on the atmosphere for moisture; ice nuclei may function in the lichens for moisture uptake. Moreover, many lichens and fungi are heat and desiccation tolerant and thus ice nuclei associated with these microbes have a longer shelf life than, for instance, bacterial ice nuclei.

The method of the present invention for increasing nucleation activity in a gas or liquid comprises the steps of: (1) obtaining a suitable lichen, fungus, fungus derived from a lichen, nuclei extracted from lichen fungi, or lichen nuclei produced by cloning ice nucleus genes from lichen fungi into bacteria or other microorganisms; (2) adding the lichen or fungus to the gas or liquid; and (3) lowering the temperature of the gas or liquid until nucleation activity occurs. The method of the invention is particularly useful for increasing ice nucleation activity in water or aqueous solutions, although the method of the invention is also useful for increasing nucleation activities in other liquids, non-aqueous liquids or solutions, or gases. As used throughout the specification and claims, the term "liquid" or "liquids" is intended to include aqueous liquids, non-aqueous liquids, and solutions, suspensions, and mixtures thereof. Likewise, the terms "gas" or "gases" are intended to include pure gases or mixtures thereof.

Preferably, the lichen or fungus is homogeneously added to the liquid or gas. This can be accomplished by grinding the lichen or fungus and then stirring it or mixing it into the gas or liquid, or by forming a liquid suspension containing the ground lichen or fungus and then introducing this suspension in the gas or liquid. Various methods for increasing the ice nucleation activity are discussed below.

In the preferred embodiment, there are several methods in which ice nuclei from lichen fungi may be used to enhance ice nucleation (i.e., to increase the temperature of freezing from $-10°$ C. to $-5°$ C. and above for water). In the first method, lichens or the lichen thallus (either collected from nature or grown in a laboratory) are ground. The resulting powder may be used directly for increasing ice nucleation activity. Alternatively, a homogenate or aqueous suspension or solution of the ground up lichen material may be utilized.

In the second method, a lichen fungus which as been isolated from the lichen association is used to increase ice nucleation activity. The fungi could be dried and ground up into a powder and/or homogenized or suspended in water.

In the third method, nuclei are extracted from a whole lichen or from a lichen fungus. This can be a crude extract, containing lichen fungus ice nuclei as well as other cell material, or it can be a pure extract of only the lichen nuclei. In a crude extract, the lichen nuclei can be particulate (still associated with solid cellular material) or in solution (separated from the cellular material). Crude extracts containing soluble ice nuclei are prepared, by, for example, grinding, homogenizing, sonicating, and centrifugation.

Nuclei in dried lichens remain active indefinitely with room temperature storage. A preservative is preferably added to liquid homogenates, extracts, etc., to prevent microbial decomposition or they could be lyophilized (freeze-dried) to get them into a dried form.

Lichens are very slow-growing in nature, so it would probably be environmentally undesirable to harvest large quantities of them from natural environments. Lichens are also slow-growing in the laboratory. They are also somewhat difficult to culture. Because many lichens and fungi derived from lichens are not easily obtained or produced, and grow very slowly both in nature and the laboratory, it may be preferable to transfer the genes coding for ice nuclei from a lichen fungus to a bacterium, yeast, filamentous fungus, or other microbe by genetic engineering techniques, common to the art, such as cloning techniques. As used throughout the specification and claims, the term "microbe" is intended to include bacteria, yeasts, filamentous fungi, and other microbes which are useful in transferring genetic coding of lichens and fungi. The microorganism into which these genes are transferred could be cultured in the laboratory and the nuclei could be used. The advantage here is that the microbe could be cultured much more easily in the laboratory. Microbes can be grown readily and more inexpensively in large amounts and thus are useful in enabling the lichen fungus nuclei to be utilized in commercial applications, such as snowmaking. The lichen fungus ice nucleation genes could be transferred to a microbe or even a plant or animal in order to induce freezing at relatively high temperatures for purposes, such as cryogenics and pest control.

The preferred lichens and lichen fungi which are useful in accordance with the invention include, but are not limited to, the genera Rhizoplaca, Xanthoparmelia, Xanthoria, Platismatia, Acarospora, Leptogium, Psora, Letharia, Peltigera, and Usnea. These lichens have an ice nucleation activity above approximately $-8°$ C. with the first three genera having an ice nucleation activity above approximately $-2°$ C. In particular, the genera Rhizoplaca, Xanthoria, Xanthoparmelia, and Lecanora are the most preferred lichens for use in accordance with the invention. These lichens have an ice nucleation activity above approximately −5° C. The above-named lichens all have a nuclei density (active at −5° C. or above) of between approximately $1 \times 10^3$ and $1 \times 10^8$ nuclei per gram lichen.

Lichens are symbiotic associations of microbes: algae (green algae and/or cyanobacteria) and fungi. Fungi or a fungus isolated from the lichen are also useful in accordance with the invention. Fungi which are particularly useful in accordance with the invention include, but are not limited to, an Antarctic endolith, Rhizoplaca Cladonia, Pertussaria, Lecanora, Phaeographis, and Acarospora.

As can be appreciated by those skilled in the art, the invention is not limited to any particular lichen or fungi. Any lichen or fungi which causes an increase in ice nucleation activity is useful in accordance with the present invention.

For snowmaking applications, the lichen, fungi, or microbe containing the genetic code of the lichen or fungi is ground and made into a slurry. The slurry is injected into a stream of water droplets in a typical snow-making machine. Alternatively, a lichen extract containing ice nuclei or a pure suspension or solution of ice nuclei is injected into a stream of droplets to be frozen. Nuclei can also be added prior to aerosolization.

For cloud seeding applications, the lichen, fungi or microbe containing the genetic code of the lichen or fungi is added to the air at an altitude which is sufficient for ice nucleation activity to occur.

The invention is further illustrated by the following non-limiting examples.

EXAMPLE 1

Sample: Lichens with a variety of growth forms (crustose, foliose, fruticose, gelatinous, and umbelliferous), sampled from a variety of substrates (rocks, trees, and soil) and from habitats with widely differing moisture contents (semiarid deserts to alpine forests) were collected from sites in the southwestern United States (see Table 1). The samples were refrigerated (5° C.) prior to testing.

TABLE I

| Sources of lichens tested for ice nucleation activity | | |
|---|---|---|
| Lichen | Habitat | Substrate |
| *Rhizoplaca chrysoleuca* | Alpine meadow | Rock-rhyolitic volcanic tuff |
| *Rhizoplaca chrysoleuca* | Semiarid desert | Rock-rhyolitic volcanic tuff |
| *Xanthoparmelia* sp. | Semiarid desert | Rock-rhyolitic volcanic tuff |
| *Xanthoria elegans* | Semiarid desert | Rock-rhyolitic volcanic tuff |
| *Platismatia* sp. | Alpine forest | Trees-*Pseudotsuga taxifolia* (Douglas fir) |
| *Acarospora* sp. | Alpine forest | Rock-andesite |
| *Acarospora* sp. | Semiarid desert | Rock-rhyolitic volcanic tuff |
| *Acarospora* sp. | Semiarid desert | Rock-sedimentary conglomerate |
| *Leptogium* sp. | Semiarid desert | Rock-silicified sedimentary breccia |
| *Psora decipiens* | Pinon-juniper woodland | Soil |
| *Xanthoparmelia* sp. | Alpine meadow | Rock-rhyolitic volcanic tuff |
| *Xanthoparmelia* sp. | Semiarid desert | Rock-sedimentary conglomerate |
| *Letharia* sp. | Alpine forest | Trees-*Pseudotsuga taxifolia* (Douglas fir) |
| *Peltigera* sp. | Alpine forest | Soil |
| *Usnea* sp. | Alpine forest | Trees-*Abies concolor* |

TABLE I-continued

| Sources of lichens tested for ice nucleation activity | | |
|---|---|---|
| Lichen | Habitat | Substrate |
| | | (white fir) |

Ice nucleation assays and activities of lichens: Ice nucleation activities of lichens were determined with an ice nucleation spectrometer. Suspensions of cell material were placed in 10-μl droplets on the surface of a paraffin-coated, temperature-controlled aluminum cold plate. As the temperature was slowly lowered (approximately 0.3° C. min$^{-1}$), the number of drops frozen was scored. Lichen suspensions were prepared by grinding lichens in a mortar and pestle, suspending them in distilled water, and homogenizing them in a ground-glass hand-operated homogenizer. Serial 10-fold dilutions were used to make suspensions ranging in density from 0.01 to 10 g (dry weight) of lichen thallus liter$^{-1}$. A minimum of 10 drops per dilution was tested. The concentrations of ice nuclei were calculated from the formula of Vali (16):$N/T = -1 \ln f/V$, where N(T) is the nucleation frequency at temperature T, f is the proportion of droplets unfrozen, and V is the volume of individual droplets. The number of nuclei per gram of lichen was calculated by dividing the concentration of nuclei per liter by the density of the lichen suspension (in grams per liter). Drops of distilled water used as controls in each nucleation spectrometer analysis always supercooled to −10° to −15° C. Other controls consisted of suspensions of INA bacteria (*P. syringae* Cit7, provided by Steven Lindow, University of California, Berkeley) and non-INA bacteria (*Escherichia coli* ATCC 8739). Suspensions of lichen substrates (rocks, tree bark, and soil) were also treated for ice nucleation activity.

Intact lichen thalli were tested for ice nucleation activity by suspending 0.1 g of lichen thallus in 3.0 ml of distilled water and chilling the suspension to −1°, −2°, −3°, −4°, −5°, −6°, or −7° C. Lichens were considered ice nucleation active at a particular temperature if the water froze within 10 minutes.

Figure 2:
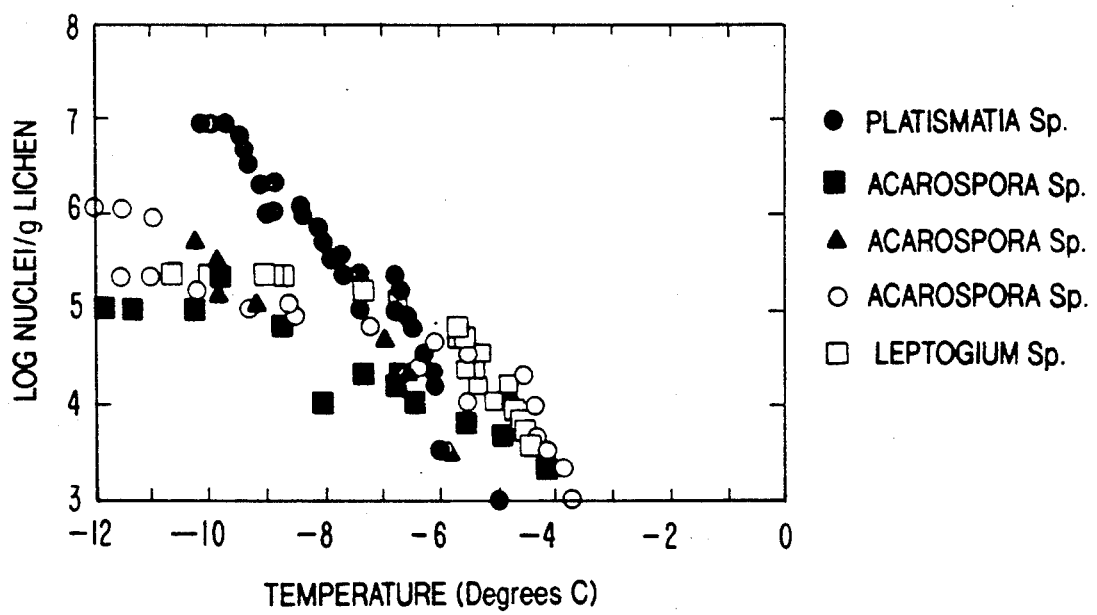
FIG. 2 is a graph of the ice nucleation spectra of certain lichens with intermediate ice nucleation activity.
Figure 3:
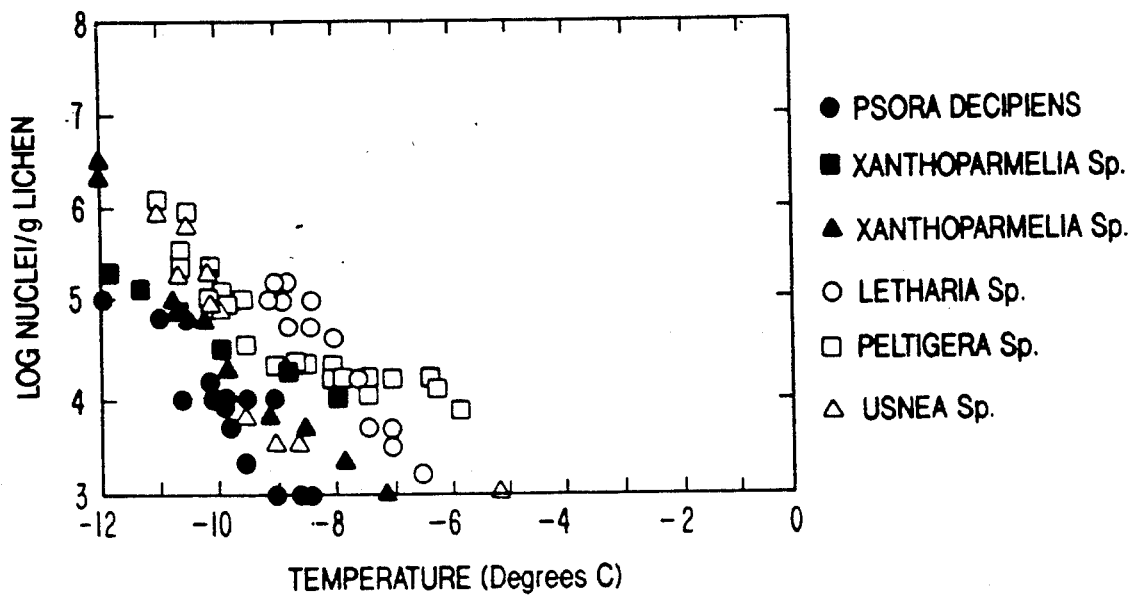
FIG. 3 is a graph of the ice nucleation spectra of certain lichens with lower ice nucleation activities.
Figure 4:
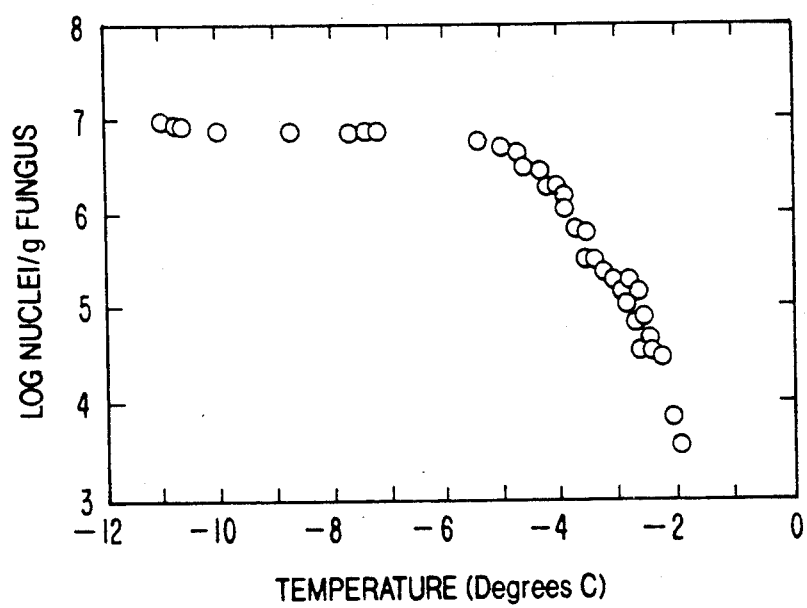
FIG. 4 is a graph of the ice nucleation spectrum of an axenic culture of the lichen fungus *Rhizoplaca chrysoleuca*.

Ice nucleation activities of lichens: Nearly all the lichens tested showed ice nucleation activity at temperatures warmer than −8° C., with several of the samples showing nucleation activity at temperatures warmer than −5° C. (FIG. 1). Of particular note were *R. chrysoleuca*, *Xanthoria elegans*, and Xanthoparmelia sp. samples, which had detectable ice nucleation activity at −3° C. or warmer and which showed nucleus densities of at least $2.3 \times 10^6$ nuclei g$^{-1}$ at −5° C. All lichens showed greater ice nucleation activity than the distilled water controls, which always supercooled to −12° C. or colder. Suspensions of lichen substrates (rocks, tree bark, and soil) tested by the same method showed little activity: less than 10% of the drops of these materials held in suspension froze at temperatures above −8° C. Lichen-associated nuclei were active at the same warm temperatures in whole lichens as in suspensions of homogenized lichen fragments, indicating that ice nucleation activity is not an artifact of thallus disruption. The ice nucleation spectra of certain lichens and a fungus is shown in the drawings. FIG. 1 is a graph of the ice nucleation spectra of certain lichens with high ice nucleation activities. FIG. 2 is a graph of the ice nucleation spectra of certain lichens with intermediate ice nucleation activity. FIG. 3 is a graph of the ice nucleation spectra of certain lichens with lower ice nucleation activities. FIG. 4 is a graph of the ice nucleation spectrum of an axenic culture of the lichen fungus *Rhizoplaca chrysoleuca*.

Heating and sonication: The heat stability of ice nuclei from the lichen *R. chrysoleuca* was tested by heating samples of a homogenized lichen suspension (0.1 g/liter in distilled water) for 10 minutes at 40°, 50°, 60°, 70°, 80°, 85°, and 95° C. These and an unheated sample were tested for ice nucleation activity by the drop-freezing assay. The effect of sonication on *R. chrysoleuca* nuclei was tested by sonicating a lichen homogenate suspension (1.0 g/liter) for 3 minutes (Branson model 250, 95-W output) at 0° C. Sonicated and nonsonicated suspensions were tested by the drop-freezing assay.

The ice nuclei of the lichen *R. chrysoleuca* were relatively heat stable; temperatures above 70° C. were required to greatly reduce ice nucleation activity (Table 2). Sonication at the intensity tested did not diminish the ice nucleation activity of *R. chrysoleuca*.

TABLE II

Effects of 10-min heat treatment on ice nucleation activity in the lichen *R. chrysoleuca*

| Temperature of heat treatment (°C.) | $T_{50}$(°C.)* |
|---|---|
| Control (no heat treatment) | −2.3 |
| 40 | −2.3 |
| 50 | −2.3 |
| 60 | −3.3 |
| 70 | −2.7 |
| 80 | −14.6 |
| 85 | −14.6 |
| 95 | −14.6 |

*$T_{50}$ Temperature at which 50% of drops froze in drop-freezing assay

Attempts to culture INA bacteria: Attempts to isolate INA bacteria from lichens showing ice nucleation activity at 31 5° C. and above were made by streaking lichen suspensions on nutrient agar and agar media selective for *P. syringae* and *E. herbicola*. The selective medium for *E. herbicola* was nutrient agar with 5% NaCl. The *P. syringae* medium (devised by Myron Sasser, University of Delaware) contained 12.0 g of sorbitol, 0.8 g of $K_2HPO_4.3H_2O$, 0.13 g of $MgSO_4.7H_2O$, 0.2 g of L-histidine, 128 mg of Cetrimide (Sigma), 100 μg of cycloheximide, 50 μg of Benomyl (Chem Service, West Chester, PA), 20 μg of Botran (Aldrich), 100 μg of rifampin, and 15 g of agar per liter of $H_2O$.

The selective medium for *P. syringae* yielded no isolates. Isolates obtained on nutrient agar amended with 5% NaCl were not of the genus Erwinia. None of the isolates from either nutrient agar or nutrient agar with 5% NaCl showed any ice nucleation activity at −5° C. when tested by the drop-freezing assay.

Ice nucleation in lichen fungal culture: An axenic culture of the lichen fungus *R. chrysoleuca*, isolated previously (2), was supplied by Vernon Ahmadjian, Clark University. The culture was grown in malt-yeast extract medium (1), suspended in distilled water, and tested for ice nucleation activity by the drop-freezing assay. The axenic culture of the mycobiont *R. chrysoleuca* showed detectable ice nucleation activity at −1.9° C. and a density of $4.5 \times 10^6$ nuclei $g^{-1}$ at −5° C. (FIG. 2).

Discussion: The relatively warm temperatures at which some of the lichen samples nucleated ice indicate a biological source of heterogeneous nuclei. The very high densities of nuclei ($10^6$ to $10^8$ nuclei $g^{-1}$) active at −5° C. in the most active of the lichens are higher than the maximum $10^3$ nuclei $g^{-1}$ observed in plant leaf tissue and the approximately $10^2$ to $10^4$ nuclei $g^{-1}$ of decaying leaf litter active at the same temperature.

The failure to culture INA bacteria from lichens suggests a nonbacterial source of lichen nuclei. The very high densities of ice nuclei associated with the most active lichens also suggest a nonbacterial source, since INA bacterial populations usually have fewer than one nucleus per cell (8,9) and the lichens typically harbor fewer than $10^5$ total bacteria $g^{-1}$ (unpublished data). Furthermore, unlike bacterial ice nucleation, which is destroyed by mild heat or sonication, the activity of lichen-associated ice nuclei resisted 70° C. heat and sonication. The evidence, therefore, points to a nonbacterial source of ice nuclei.

Organic and inorganic dust particles, including clay minerals, all of which only show freezing nucleation at temperatures below −8° C. (8,9), are not likely candidates as lichen-associated ice nuclei. Moreover, nuclei of this nature would not be found concentrated only on lichens. Thus, having eliminated bacterial and dust-derived nuclei, one must conclude that the ice nucleation activity of these lichens is the result of a substrate produced by the lichens themselves. This substance could be a product of the phycobiont, the mycobiont, or a combination of the two.

The presence of ice nuclei active at relatively warm temperatures in the axenic fungus *R. chrysoleuca* points to the mycobiont as the source of ice nuclei and further underscores the nonbacterial source of these nuclei (see FIG. 4). found in INA bacteria. Alternatively, one or more of the secondary metabolites occurring as precipitates on the surfaces of lichen hyphae may be the source of the observed ice nuclei.

EXAMPLE 2

Mycobionts (lichen fungi) and phycobionts (lichen algae) were tested in accordance with Example I. Results are shown in Tables III and IV. Some of the mycobionts showed an ice nucleation activity of above −5° C. The phycobionts showed no ice nucleation activity above −5° C.

TABLE III

Ice Nucleation Activity (INA) of Certain Mycobionts

| Mycobionts | Nuclei/g at −5° C. | Warmest INA (°C.) |
|---|---|---|
| *Antarctic endolith* | | −5.9 |
| *Cladonia bellidiflora* | | −8.3 |
| *Pertussaria flavicans* | $3.1 \times 10^4$ | −4.1 |
| *Lecanora dispersa* | $9.7 \times 10^3$ | −4.6 |
| *Phaeographis leucochelia* | | −8.3 |
| *Cladonia chlorophaea* 1429 | | −10.0 |
| *Cladonia pleurota* | | −9.1 |
| *Acarospora fuscata* | | −9.1 |
| *Cladonia subcariosa* | | −6.2 |
| *Cladonia boryi* | $8.3 \times 10^3$ | −5.0 |
| *Cladonia cristatella* 113 | | −6.3 |
| *Cladonia cariosa* | | −6.3 |
| *Cladonia rangiferina* | $5.7 \times 10^3$ | −5.0 |

TABLE IV

Ice Nucleation Activity (INA) of Certain Phycobionts

| Phycobionts | Nuclei/g at −5° C. | Warmest INA (°C.) |
|---|---|---|
| Nostoc from *Peltigera canina* | | −9.1 |
| Nostoc from *Peltigera rufescens* | | −7.5 |
| Nostoc from *Peltigera spuria* | | −9.1 |
| *Trebouxia erici* | | −9.2 |
| Trebouxia from *Parmeliopsis hyperopta* | | −6.3 |
| Trebouxia from *Acarospora fuscata* | | −5.1 |

TABLE IV-continued

| Ice Nucleation Activity (INA) of Certain Phycobionts | | |
|---|---|---|
| Phycobionts | Nuclei/g at −5° C. | Warmest INA (°C.) |
| Trebouxia from *Lecanora dispersa* | | −5.9 |
| Trebouxia from *Aspicilia calcarea* | | −6.3 |
| Trebouxia from *Stereocaulon saxatile* | | −8.8 |
| *Coccomyxia peltigerae* var *variolosa* | | −8.3 |
| Trebouxia from *Parmelia tinctorum* | | −16.0 |
| Trebouxia from *Lecidea tumida* | | −6.2 |
| Trebouxia from *Cladonia coniocraea* | | −11.3 |

Although the invention has been described with reference to these preferred embodiments, other embodiments can achieve the same results. Various and modifications of the present invention will be obvious to those skilled in the art and it is intended to cover in the appended claims all such modifications and equivalents.

What is claimed is:

1. A method for increasing ice nucleation activity of an aqueous liquid comprising
   adding a suitable member selected from the group consisting of lichens, fungi derived from lichens, ice nuclei derived from lichens, and ice nuclei derived from fungi derived from lichens
   to the aqueous liquid; wherein the temperature at which ice nucleation activity occurs is at a temperature above a temperature at which ice nucleation activity occurs for the aqueous liquid without the selected suitable member.

2. The method of claim 1 wherein the selected suitable member comprises a lichen selected from the group consisting of the genera Rhizoplaca, Xanthoparmelia, Xanthoria, Platismatia, Acarospora, Leptogium, Psora, Letharia, Peltigera, and Usnea.

3. The method of claim 1 wherein the selected suitable member comprises a lichen fungus selected from the group consisting of the genera Rhizoplaca, Xanthoparmelia, Xanthoria, Platismatia, Acarospora, Leptogium, Psora, Letharia, Peltigera, and Usnea.

4. The method of claim 1 wherein the selected suitable member comprises a fungus selected from the group consisting of an Antarctic endolith, Rhizoplaca Cladonia, Pertussaria, Lecanora, Phaeographis, and Acarospora.

5. The method of claim 1 further comprising the step of lowering the temperature of the liquid containing the selected suitable member until ice nucleation activity occurs.

6. The method of claim 1 wherein the temperature at which ice nucleation activity occurs is substantially above the temperature at which ice nucleation activity occurs for the liquid without the selected suitable member.

7. The method of claim 1 wherein ice nucleation activity occurs at above approximately −10° C.

8. The method of claim 7 wherein ice nucleation activity occurs at above approximately −5° C.

9. The method of claim 1 wherein the selected suitable member has a nuclei density of above approximately $1 \times 10^3$ nuclei per gram.

10. The method of claim 1 wherein the selected suitable member is distributed uniformly throughout the aqueous liquid.

11. The method of claim 10 wherein the selected suitable member is added to the aqueous liquid in at least one form selected from the group consisting of an aqueous suspension and an aqueous solution.

12. The method of claim 10 wherein the selected suitable member is ground prior to adding it to the aqueous liquid.

* * * * *